United States Patent
Coggan et al.

(10) Patent No.: US 7,214,644 B2
(45) Date of Patent: May 8, 2007

(54) CROSS-COUPLING REACTIONS

(75) Inventors: Jennifer A. Coggan, Ontario (CA); Nan-Xing Hu, Ontario (CA); H. Bruce Goodbrand, Ontario (CA); Timothy P. Bender, Ontario (CA)

(73) Assignee: Xerox Corporation, Stamford, CT (US)

( * ) Notice: Subject to any disclaimer, the term of this patent is extended or adjusted under 35 U.S.C. 154(b) by 11 days.

(21) Appl. No.: 10/903,138

(22) Filed: Jul. 30, 2004

(65) Prior Publication Data

US 2006/0025303 A1 Feb. 2, 2006

(51) Int. Cl.
*B01J 23/72* (2006.01)

(52) U.S. Cl. .................. 502/331; 423/22; 423/32; 423/33; 423/42; 423/140; 75/351; 75/371; 75/721; 75/739; 75/740; 75/741; 420/457; 420/461; 420/462; 420/464; 420/466; 420/485; 420/497; 420/500

(58) Field of Classification Search ............. 502/150, 502/331; 423/22, 32, 33, 42, 140; 75/351, 75/371, 721, 739, 740, 741; 420/457, 461, 420/462, 464, 466, 485, 497, 500
See application file for complete search history.

(56) References Cited

U.S. PATENT DOCUMENTS

| 4,590,177 A | 5/1986 | Richard et al. | |
|---|---|---|---|
| 4,705,765 A | 11/1987 | Lewis | |
| 4,740,490 A | 4/1988 | Vanderspurt et al. | |
| 4,900,705 A * | 2/1990 | Sawicki et al. | 502/158 |
| 5,093,513 A * | 3/1992 | Sawicki et al. | 558/277 |
| 5,202,519 A * | 4/1993 | Khare | 585/741 |
| 5,276,233 A * | 1/1994 | Blom et al. | 585/419 |
| 5,286,354 A * | 2/1994 | Bard et al. | 205/551 |
| 6,090,746 A | 7/2000 | Bonnemann et al. | |
| 6,559,243 B1 * | 5/2003 | Heinzman et al. | 525/398 |
| 6,610,195 B2 * | 8/2003 | Masloboishchikova et al. | 208/137 |

FOREIGN PATENT DOCUMENTS

| EP | 00476765 | 6/1997 |
|---|---|---|
| GB | 1493810 | 11/1977 |
| JP | 10309466 | 10/1997 |
| JP | 11288940 | 10/1999 |
| JP | 03160876 | 6/2003 |

OTHER PUBLICATIONS

Fitton et al., J. Organomet. Chem., 1971, 28, pp. 287-291.
Dufaud et al., J. Chem. Soc. Chem. Commun., 1990, pp. 426-427.
Thathagar et al., J. Am. Chem. Soc. 2002, 124 pp. 11858-11859.
Bradley J. S. et al. "Surface Spectroscopic study of the stabilization mechanism for shape-selectively synthesized nanostructured transition metal colloids"—JACSA May 17, 2000, 122/19 pp. 4631-4636 Abstract.
Bender et al., Chem. Mater. 2001, 13, pp. 4105-4111.

* cited by examiner

*Primary Examiner*—C. Melissa Koslow
(74) *Attorney, Agent, or Firm*—Pillsbury Winthrop Shaw Pittman, LLP

(57) ABSTRACT

A method for producing a copper/palladium colloid catalyst useful for Suzuki couplings.

15 Claims, No Drawings

CROSS-COUPLING REACTIONS

BACKGROUND

Disclosed is a process for the preparation of a colloid catalyst.

The Suzuki reaction for cross-coupling of organic electrophiles, such as aryl halides, diazonium salts or triflates, with boronic acids or boronate esters is a reaction utilized in the formation of carbon-carbon bonds in the synthesis of organic compounds such as biaryls, as illustrated below. The reaction is also employed in the synthesis of agrochemicals, polymers, and pharmaceutical intermediates. The Suzuki reaction may also be utilized in the preparation of charge transporting molecules such as triarylamines. For example, the reaction may be used to prepare hole transporting molecules for photoreceptors and organic light emitting diodes ("OLEDs").

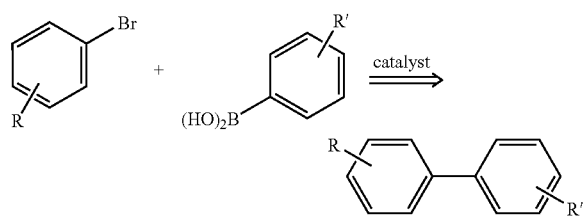

Exemplar Suzuki Reaction

The Suzuki catalyst of choice may be a palladium(0) complex in the presence of phosphorus ligands, examples of which are $Pd(dppf)_2$ or $Pd(PPh_3)_4$. The high cost of palladium makes the process for preparing organic compounds using this reaction expensive. This expense is compounded by clean-up costs associated with removing palladium residues due to spent catalysts from the product. These catalysts also have the disadvantage that they are extremely sensitive to oxidation and are difficult to use industrially because of their reduced shelf life, particularly as solutions. Furthermore, such compounds are very sensitive to heat, so that reactions of relatively unreactive aromatics at elevated temperatures result in rapid deactivation of the catalyst with precipitation of palladium black (Fitton et al., *J. Organomet. Chem.*, 1971, 28, 287–291, Dufaud et al., *J. Chem. Soc. Chem. Commun.*, 1990, 426–427). Aryl nickel chlorides have also been reported as a useful catalyst but may pose exposure hazards.

REFERENCES

Improved colloid catalysts comprising palladium—Pt and/or Ru and/or Cu mixtures are described in *J. Am. Chem. Soc.* 2002, 124, 11858–11959 for use in the Suzuki reaction. The paper describes that such colloid catalysts may be used as a Suzuki catalyst. Of the bimetallic colloid catalyst combinations cited therein, Cu/Pd is reported to be most active in the coupling of phenylboronic acid and iodobenzene to give biphenyl (on par with pure Pd). While noting that palladium(0) complex in the presence of (phosphorus) ligands is a catalyst of choice in Suzuki reactions, no direct comparison is made in the paper to such catalyst.

A Cu:Pd catalyst is also described in Japanese Publication No. 03160876 JP. Such catalyst is described as useful for electroless plating to simplify the process of forming metal plating patterns of an electroless metal plated film. The catalyst for electroless plating includes a colloid of an alloy which consists of one selected from the first group consisting of Pd and Pt, and at least one selected from the second group consisting of Ag and Cu.

Preparation of the nanocolloids of *J. Am. Chem. Soc.* 2002, 124, 11858–11959 is described in the paper (in published "supporting papers" as referenced in the article) as entailing mixing homogeneous stock solutions of the metal chloride precursors followed by subsequent reduction with tetraoctylammonium formate ("TOAF") in dimethylformamide ("DMF"). The nanocluster catalysts are reported to be formed by placing the metal chloride in dimethylformamide ("DMF") into a Schlenk-type vessel equipped with a rubber septum and magnetic stirrer which has been evacuated and refilled with $N_2$. Tetraoctylammonium formate ("TOAF") in dimethylformamide ("DMF") is then added to the solution and heated to at 65° C. and the mixture stirred for 24 hours under a slight overpressure of $N_2$. It is indicated that the color of the mixture changes when the colloidal suspension is formed. Such suspension is then stored under $N_2$.

Tetraoctylammonium formate ("TOAF") is described as being prepared by a modification of the method Masse, *Ph.D. Thesis*, Verlag Mainz, Aachen, 1999, ISBN 3089653-463. The tetraoctylammonium formate ("TOAF") preparation process involves exchange of tetra-n-polyammonium bromide ("TOAB") with formic acid through the use of an ion-exchange resin and is relatively complex. The ion-exchange resin is suspended in a sodium hydroxide solution and charged to a column that is subsequently flushed with NaOH. The column is then flushed with distilled water followed by formic acid solution, distilled water and methanol. The resin is allowed to swell for 1 hour and the column subsequently flushed with a solution of tetra-n-octylammonium bromide ("TOAB") in methanol until the elute tests positive for chloride using $AgNO_3$. The appropriate methanol fraction is evaporated on a rotavapor and the crude tetraoctylammonium formate ("TOAF") (light oil) dried for 24 hours under vacuum. A stock solution of tetraoctylammonium formate ("TOAF") in dimethylformamide ("DMF") is used for the synthesis of the colloid.

This method can be extremely time consuming in that the preparation time for the catalyst is lengthy. It may take a day or more to prepare the resin, and the resin would have to be regenerated before use each time. The expense of the resin may be $100–$500 per kg of resin, and at least twenty times the amount of resin per gram of material to be exchanged would have to be used.

SUMMARY

Aspects disclosed herein include:
a formate salt, a copper metal salt and a metal salt other than copper in a reaction mixture to form a copper:metal colloid catalyst, and
a method comprising forming a copper:metal colloid catalyst under an inert atmosphere in a solution comprising at least one copper salt and at least one palladium salt a reducing reagent in an amount capable of reducing said copper salt and said palladium salt.

DETAILED DESCRIPTION

In embodiments it is illustrated a method for preparing colloid catalysts as described in *J. Am. Chem. Soc.* 2002, 124, 11858–11959 without the need for the isolated formation of tetraoctylammonium formate ("TOAF") through the employment of an ion-exchange resin. It is further a embodiment to be able to reduce to one simple reaction the laborious multi-step process for forming the colloid catalysts set forth in *J. Am. Chem. Soc.* 2002, 124, 11858–11959. Colloid catalysts of metal salts, such as described in *J. Am. Chem. Soc.* 2002, 124, 11858–11959, can be formed without the laborious tasks of first producing tetraoctylammonium formate ("TOAF"), which is instead prepared in situ.

Colloid catalysts produced by such methods may be utilized for numerous cross-coupling reactions, including but not limited to Suzuki, Stille, Heck, Sonagashira, Negishi, Ullmann, Grignard cross-coupling, Buchwald-Hartwig amination, and catalytic ether formation.

In an embodiment, a method is provided comprising mixing in one solution comprising organic solvent, a phase transfer catalyst, a formate salt in a molar ratio from about 0.25 to about 5.0 or from about 0.5 to about 2.5 to the phase transfer catalyst, and at least one salt of copper, other metal salt or mixture thereof in a concentration of from about 0.0001 to about 8 equivalents or alternatively from about 0.0001 to about 2 equivalents, or alternatively from about 0.001 to about 0.8 equivalents, to the mixture. The method may also comprise heating the one solution to a temperature from about 40° C. to about 100° C. to form a copper:metal salt colloid catalyst. The temperature may also be from about 55° C. to about 70° C. The formate salt may be selected from at least one of lithium formate, sodium formate, potassium formate, cesium formate, a $NR_1R_2R_3R_4$ formate where $R_1$, $R_2$, $R_3$, and $R_4$ are independently hydrogen, or a $C_2$–$C_{18}$ hydrocarbon, or $PR_1R_2R_3R_4$ formate where $R_1$, $R_2$, $R_3$, and $R_4$ are independently hydrogen, or $C_2$–$C_{18}$ hydrocarbon. The phase transfer catalyst is a $NR_1R_2R_3R_4$ halide where $R_1$, $R_2$, $R_3$, and $R_4$ are independently hydrogen or a $C_2$–$C_{18}$ hydrocarbon. The phase transfer catalyst may be tetraoctylammonium halide. At least one of the salts may be $CuCl_2$. At least one of the metals of said metal salt(s) may be selected from at least one of: nickel, ruthenium, rhodium, palladium, silver, osmium, iridium, platinum and gold, or at least one of the metals of said metal salt(s) is selected from at least one of: platinum, palladium and ruthenium. The metal of the metal salt(s) may be palladium. The metal salt(s) may comprise $PdCl_2$. The organic solvent may comprise dimethylformamide. The formate salt may be ammonium formate.

In another embodiment, a method is provided which comprises forming of a reducing agent for reducing at least one copper salt and at least one palladium salt in a solution comprising at least one copper salt and at least one palladium salt while keeping the solution under an inert atmosphere. The method may also comprise heating the solution to a temperature from about 40° C. to about 100° C., or about 55° C. to about 70° C. to form a copper:palladium colloid catalyst. The reducing reagent may be formed by reaction of formate salt and a phase transfer catalyst, and may be TOAF formed in situ.

In an alternate embodiment, a method comprising forming a reducing agent for reducing a metal salt and a copper salt in a solution comprising an organic solvent, said metal salt and said copper salt, while keeping the solution under an inert atmosphere. The method may further comprise heating the solution to a temperature from about 40° C. to about 100° C., or about 55° C. to about 70° C. to form a nanocolloid catalyst. The reducing reagent may be formed by reaction of a formate salt and a phase transfer catalyst and may be TOAF formed in situ. The formate salt may be selected from at least one of lithium formate, sodium formate, potassium formate, cesium formate, or a $NR_1R_2R_3R_4$ formate wherein $R_1$, $R_2$, $R_3$, and $R_4$ are independently hydrogen, or a $C_2$–$C_{18}$ hydrocarbon, or $PR_1R_2R_3R_4$ formate wherein $R_1$, $R_2$, $R_3$, and $R_4$ are independently hydrogen, or $C_2$–$C_{18}$ hydrocarbon. The phase transfer catalyst is a $NR_1R_2R_3R_4$ halide wherein $R_1$, $R_2$, $R_3$, and $R_4$ are independently hydrogen, or a $C_2$–$C_{18}$ hydrocarbon, and may be tetraoctylammonium halide. The organic solvent may comprise dimethylformamide. The formate salt may be animonium formate. The metal of said metal salt may be selected from at least one of: nickel, ruthenium, rhodium, palladium, silver, osmium, iridium, platinum and gold, or platinum, palladium and ruthenium. The metal salt may be $CuCl_2$ or $PdCl_2$.

Colloid catalysts may be prepared by contemporaneously admixing a formate salt wherein the formate salt is comprised of lithium, sodium, potassium, cesium, $NR_1R_2R_3R_4$ formate, wherein $R_1$, $R_2$, $R_3$, and $R_4$ may be chosen independently from hydrogen, or a hydrocarbon containing from about 2 to about 18 carbons, $PR_1R_2R_3R_4$ formate wherein $R_1$, $R_2$, $R_3$, $R_4$ may be independently chosen from hydrogen, or a hydrocarbon containing from about 2 to about 18 carbons, a phase transfer catalyst comprising a $NR_1R_2R_3R_4$ halide wherein $R_1$, $R_2$, $R_3$, $R_4$ may be chosen independently from hydrogen or a hydrocarbon containing from about 2 to about 18 carbons (such as tetraoctylammonium bromide), and a metal salt, including a copper salt and a non-copper metal salts containing the metals Ni, Pd, Pt, Rh, Ir, Ru, Os and the like. The catalyst may be produced in amounts sufficient to effectuate the catalytic cycle of the Suzuki reaction, viz., an oxidative addition-transmetallation-reductive elimination sequence.

The formate salt may be selected from at least one of lithium formate, sodium formate, potassium formate, cesium formate, or a $NR_1R_2R_3R_4$ formate wherein $R_1$, $R_2$, $R_3$, and $R_4$ are independently hydrogen, or a $C_2$–$C_{18}$ hydrocarbon such as ammonium formate, or PR1R2R3R4 formate wherein $R_1$, $R_2$, $R_3$, and $R_4$ are independently hydrogen, or $C_2$–$C_{18}$ hydrocarbon. The phase transfer catalyst is a $NR_1R_2R_3R_4$ halide wherein $R_1$, $R_2$, $R_3$, and $R_4$ are independently hydrogen or a $C_2$–$C_{18}$ hydrocarbon. The phase transfer catalyst may be tetraoctylammonium halide. At least one copper salt may be $CuCl_2$. At least one palladium salt may be $PdCl_2$. The solution may comprise dimethylformamide. The concentration of formate salt in the reaction mixture may be in a mole ratio from about 0.25 to about 5.0, or a mole ratio from about 0.5 to about 2.5 to the phase transfer catalyst. At least one salt of copper, other metal salt, or mixture thereof may be added in an amount from about 0.0001 equivalents to about 0.8 equivalents or from about 0.001 to about 0.08 equivalents. The temperature of the reaction mixture may be from about 40° C. to about 100° C. or from about 50° C. to about 70° C.

A particularly useful colloid catalyst that may be used in performing Suzuki reactions that may be produced by the method described herein is a 50%:50% Cu/Pd catalyst which can provide the same yield as a palladium(0) complex in the presence of phosphorous ligands, such as tetrakis(triphenylphosphine)palladium.

EXAMPLE I

Preparation of the Catalyst

Dimethylformamide ("DMF") is placed in a flask under argon. To the flask was added 1.0 equivalent of ammonium formate, 1.0 equivalent of tetraoctylammonium bromide and 0.4 equivalents total of $CuCl_2$ and $PdCl_2$. The mixture is then heated at 65° C. for from about 8 to about 24 hours, followed by cooling. The colloid catalyst can be used directly in the Suzuki reaction.

Model Reaction

The catalyst prepared above was used in a model Suzuki reaction, the coupling of bromobenzene and phenylboronic acid in dimethylformamide ("DMF") with $K_2CO_3$ at 100° C. from about 8 to about 24 hours. When the 50% Cu/50% Pd catalyst was compared to tetrakis(triphenylphosphine)palladium (2 mol %), similar yields of the biphenyl product approaching 100% was noted.

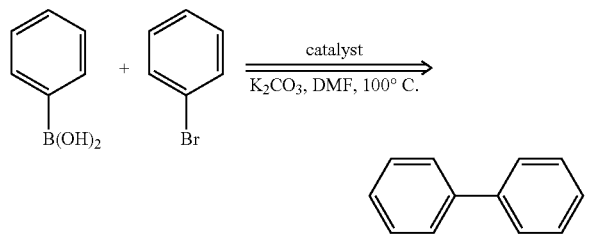

EXAMPLE II

The synthesis of N,N-(3,4-dimethylphenyl)-4-aminobiphenyl, a well-known hole transporting material ("HTM", ((Bender et al, Chem. Mater. 2001, 13, 4105–4111) utilized in photoreceptors, may be performed by the coupling of the appropriate bromo triarylamine with phenylboronic acid with subsequent creation of a biaryl system through the use of a Suzuki reaction.

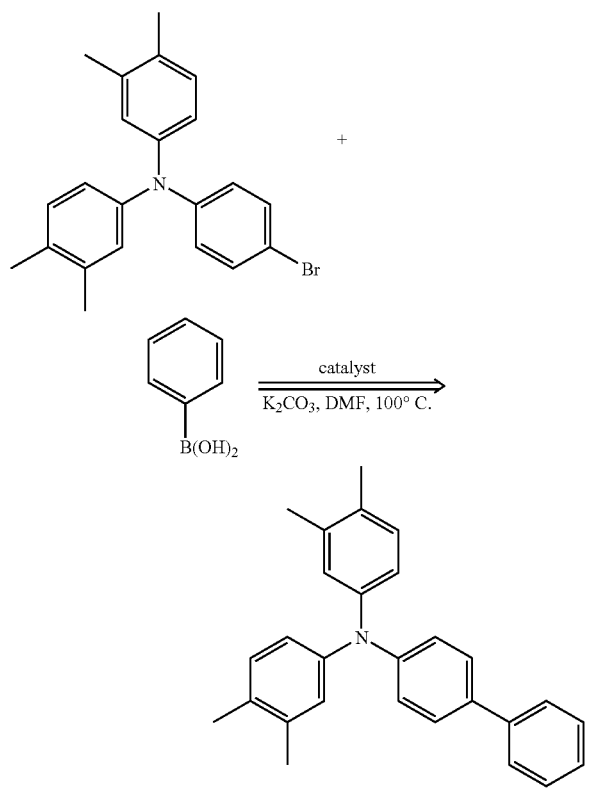

I

N,N-(3,4-dimethylphenyl)-4-bromoaniline (0.38 g) in a concentration 160 mM was reacted with phenylboronic acid (0.183 g) in a concentration of 240 mM in the presence of 0.412 g potassium carbonate and 10 mL of dimethylformamide ("DMF") at 100° C. for 8–24 hours with 6 mL of the colloid catalyst solution (2 mol %) (3 different catalysts with increasing amounts of palladium) to prepare N,N-(3-4-dimethylphenyl)-4-aminobiphenyl. Comparison was made in respect of product yield with a commercially available tetrakis(triphenylphosphine)palladium catalyst. Each catalyst was used at 2 mol percent in each of the reactions. The results are shown in Table I. As can be seen, the percentage of product versus starting material for 50% Pd:50% Cu colloid was found to be nearly equivalent to that of $Pd(PPh_3)_4$ (74% v. 76%).

TABLE I

| Type of Catalyst | % Starting Material | % Product |
|---|---|---|
| 5% Pd:95% Cu colloid | 80.5 | 19.5 |
| 25% Pd:75% Cu colloid | 71 | 29 |
| 50% Pd:50% Cu colloid | 26 | 74 |
| $Pd(PPh_3)_4$ | 24 | 76 |

Reaction conditions, such as reaction temperature, solvent, catalyst may be optimized in any particular Suzuki reaction, and the optimum amount of palladium in the Cu/Pd colloid catalyst may vary somewhat between reaction schemes.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method comprising:
   mixing an organic solvent, a phase transfer catalyst, a formate salt, a copper metal salt, and a non-copper metal salt in a reaction mixture to form a copper:metal colloid catalyst,
   wherein the formate sale and the phase transfer catalyst react in situ within the reaction mixture to form a reducing agent, and the reducing agent reduces the copper and non-copper metal salts;
   wherein said phase transfer catalyst is a compound of the formula $NR_1R_2R_3R_4$ halide wherein $R_1$, $R_2$, $R_3$, $R_4$ are independently hydrogen or a $C_2$–$C_{18}$ hydrocarbon.

2. A method in accordance with claim 1, wherein said formate salt is in a molar ratio of from about 0.25 to about 5 to said phase transfer catalyst.

3. A method in accordance with claim 1, wherein said copper metal salt and/or non-copper metal salt are in a concentration from about 0.0001 to about 8 molar equivalent in said reaction mixture.

4. A method in accordance with claim 1, further comprising heating said reaction mixture to a temperature from about 40° C. to about 100° C.

5. A method in accordance with claim 4, wherein said temperature is from about 55° C. to about 70° C.

6. A method in accordance with claim 1, wherein said formate salt is one or more of lithium formate, sodium formate, potassium formate, cesium formate, or a $NR_1R_2R_3R_4$ formate wherein $R_1$, $R_2$, $R_3$, and $R_4$ are independently hydrogen, or a $C_2$–$C_{18}$ hydrocarbon, or $PR_1R_2R_3R_4$ formate where $R_1$, $R_2$, $R_3$, and $R_4$ are independently hydrogen, or $C_2$–$C_{18}$ hydrocarbon.

7. A method in accordance with claim 1, wherein said copper salt is $CuCl_2$.

8. A method in accordance with claim 1, wherein said non-copper metal salt comprises a metal selected from a group consisting of nickel, ruthenium, rhodium, palladium, silver, osmium, iridium, platinum and gold.

9. A method in accordance with claim 8, wherein said metal is platinum, palladium and ruthenium.

10. A method in accordance with claim 1, wherein said non-copper metal salt is a palladium salt.

11. A method in accordance with claim 10, wherein said metal salt is $PdCl_2$.

12. A method in accordance with claim 1, wherein said organic solvent comprises dimethylformamide.

13. A method in accordance with claim 1, wherein said formate salt is ammonium formate.

14. A method in accordance with claim 1, wherein said phase transfer catalyst is tetraoctylanimonium halide.

15. A method according to claim 1, the reducing agent formed in situ within the reaction mixture is tetraoctylanimonium formate.

* * * * *